(12) United States Patent
Tsukada et al.

(10) Patent No.: US 6,530,901 B1
(45) Date of Patent: Mar. 11, 2003

(54) PORTABLE PAINKILLING SYSTEM

(75) Inventors: Osamu Tsukada, Nagano (JP);
Yasuhiko Nakajima, Kanagawa (JP)

(73) Assignee: Tsukada Medical Research Co., Ltd., Tokyo (JP)

( * ) Notice: Subject to any disclaimer, the term of this patent is extended or adjusted under 35 U.S.C. 154(b) by 0 days.

(21) Appl. No.: 09/806,347

(22) PCT Filed: Jul. 29, 1999

(86) PCT No.: PCT/JP99/04068

§ 371 (c)(1),
(2), (4) Date: Mar. 29, 2001

(87) PCT Pub. No.: WO01/08728

PCT Pub. Date: Feb. 8, 2001

(51) Int. Cl.$^7$ .......................... A61M 37/00; A61M 1/00; A61K 9/22
(52) U.S. Cl. ..................... 604/132; 604/153; 604/890.1
(58) Field of Search .............................. 604/6.11, 9, 30, 604/118, 131, 132, 151, 153, 183, 187, 288.03, 288.04, 890.1

(56) References Cited

U.S. PATENT DOCUMENTS

| | | | |
|---|---|---|---|
| 3,827,439 A | * 8/1974 | Schulte et al. | 251/342 |
| 4,588,394 A | * 5/1986 | Schulte et al. | 604/185 |
| 4,781,680 A | * 11/1988 | Redmond et al. | 604/185 |
| 4,801,292 A | * 1/1989 | Watson | 604/185 |
| 5,683,369 A | * 11/1997 | Tsukada | 604/133 |
| 5,836,940 A | * 11/1998 | Gregory | 604/20 |
| 5,891,102 A | * 4/1999 | Hiejima et al. | 604/185 |

FOREIGN PATENT DOCUMENTS

| | | |
|---|---|---|
| JP | 62-11465 | 1/1987 |
| JP | 9-285539 | 11/1997 |

\* cited by examiner

Primary Examiner—Henry C. Yuen
Assistant Examiner—John Fristoe
(74) Attorney, Agent, or Firm—Sughrue Mion, PLLC

(57) ABSTRACT

A portable painkilling system comprises: a first continuous injector (1) for liquid medicine which continuously discharges liquid medicine through a control path (131) in an outlet portion (13) for a given period of time; a flexible, elastic reservoir (3) connected to the outlet portion (13) of the first continuous injector (1) for liquid medicine at one end thereof, the reservoir (3) being adapted to constrict in a normal condition and to expand when liquid medicine from the first continuous injector (1) is being charged into the reservoir (3) so as to contain a maximum quantity of liquid medicine; and a second continuous injector (2) for liquid medicine having an inlet portion (22) connected to the other end (32) of the reservoir (3), the second continuous injector (2) being adapted to receive liquid medicine from the reservoir (3) and to continuously discharge liquid medicine stored in the second continuous injector (2) through a control path (231) in an outlet portion (23) for a given period of time.

9 Claims, 8 Drawing Sheets

PORTABLE PAINKILLING SYSTEM

TECHNICAL FIELD

This invention relates to a portable painkilling system which is attached to a patient's body.

Analgesics play an important role in pain control and in cases involving chronic pain. It has heretofore been necessary for a patient to be hospitalized or visit a hospital as an out-patient for a long time.

BACKGROUND ART

The need for frequent injection of liquid medicine such as an analgesic or the like is onerous both to a patient and to a hospital in terms of time and efficiency. Consequently, an automatic injection system has been developed which injects liquid medicine to a patient periodically and automatically. However, a conventional system is large and expensive, and it physically limits a patient. Thus, a convenient automatic injection system which does not physically limit an action of a patient and can be applied to in-patients, out-patients, and home-patients has been desired for a long time.

In order to respond to this demand, the present applicant has previously proposed a portable analgesic system (see International Application No. PCT/JP 94/00608: International Public Disclosure No. WO 95/27521). This portable analgesic system comprises: a continuous injector for liquid medicine which continuously discharges liquid medicine through a control path in an outlet portion for a given period of time; a switch-valve detachably connected to an outlet of the injector for shutting off discharge of liquid medicine from the injector; a three-way connector connected to an outlet of the switch valve and having three ways; a flexible, elastic reservoir detachably connected to an end of the three-way connector, the reservoir being adapted to constrict in a normal condition and to expand when liquid medicine from the injector is being charged into the reservoir so as to contain a given quantity of liquid medicine; and a pressure-check valve connected to another way of the three-way connector for opening a flow passage only when a pressure of liquid medicine in the reservoir rises above a given value.

In this portable analgesic system, a continuous injector for liquid medicine having a given volume and a given continuous period of time is prepared beforehand. The continuous injector is charged with a given amount of liquid medicine (3 to 5 cubic centimeters) in accordance with a symptom of a patient. Then, the switch valve is opened and liquid medicine is transferred from the continuous injector to the reservoir over a given long period of time (about 0.5 to 10 hours). A patient can move freely during transfer of liquid medicine, while wearing the system. Duration of transferring liquid medicine from the injector to the reservoir substantially accords with duration of continuing an effect of liquid medicine. When a patient feels a pain, the patient presses the reservoir by oneself to inject liquid medicine from the reservoir through the pressure-check valve to the interior of the patient's body.

However, since in this portable analgesic system, a pressure and a period of time required for pressing the reservoir are about 350 to 700 mm Hg and about 20 to 200 seconds, respectively, a tired patient needs to work hard. Also, if a patient stops pressing the reservoir in the course of pressing, a medical licensee cannot know how much of the liquid medicine has been injected from the reservoir into the patient's body. Consequently, it is difficult to control the supply of liquid medicine.

In order to overcome this problem, the present applicant has further proposed a portable analgesic system (see International Application No. PCT/JP 99/02699: International Public Disclosure No. WO 00/71190). This portable analgesic system comprises: a continuous injector for liquid medicine which continuously discharges liquid medicine through a control path in an outlet portion for a given period of time; a three-way connector connected to an outlet of the injector and having three ways; a reservoir detachably connected through a flexible tube to an middle end of the three-way connector, the reservoir being adapted to constrict in a normal condition and to expand when another liquid medicine from the injector is being charged into the reservoir so as to contain liquid medicine; and an ON-OFF clamp connected to the flexible tube for clamping and releasing the flexible tube to close and open a flow passage; and a switch valve detachably connected to the other end of the three-way connector for shutting off any discharge of liquid medicine from the injector.

A current portable analgesic system acts effectively in the case where liquid medicine should be injected, at relatively frequent times, into a patient in severe pain. However, in the case where liquid medicine is injected, several times during a relatively long period of time, into a patient in relatively mild pain, a medical licensee or a patient will encounter a new problem, that is, the sterilizing and disinfecting when charging liquid medicine into a continuous injector for liquid medicine or a reservoir is troublesome. In view of the psychology of a patient suffering from pain, it will be effective in medical treatment for him/her to obtain relief and contentment by pressing the reservoir by him/herself.

DISCLOSURE OF THE INVENTION

An object of the present invention is to provide a convenient and portable painkilling system which is attached to a patient's body and can inject liquid medicine into a patient as many times as required by a patient without the need for sterilizing and disinfecting.

A portable painkilling system in accordance with the present invention comprises: a first continuous injector for liquid medicine which continuously discharges liquid medicine through a control path in an outlet portion for a given period of time; a flexible, elastic reservoir connected to the outlet portion of the first continuous injector for liquid medicine at one end thereof, the reservoir being adapted to constrict in a normal condition and to expand when liquid medicine from the first continuous injector is being charged into the reservoir so as to contain a maximum quantity of liquid medicine; and a second continuous injector for liquid medicine having an inlet portion connected to the other end of the reservoir, the second continuous injector being adapted to receive liquid medicine from the reservoir and to continuously discharge liquid medicine stored in the second continuous, injector through a control path in an outlet portion for a given period of time.

The reservoir in the present invention may be any one of various kinds of reservoirs such as a syringe type reservoir, a bag type reservoir, a bellows type reservoir, a circular button type reservoir, a dome type reservoir, a multi-stepped, button type reservoir, a tandem chamber type reservoir, or the like.

The first and second continuous injectors for liquid medicine which have given volumes and continuous discharge period of time, respectively, the reservoir having a give volume, and the male lure connector are prepared for assembling. The first continuous injector for liquid medicine, the reservoir, and the second continuous injector for liquid medicine are connected in series one after another. A medical licensee charges desired liquid medicine into the first continuous injector by a given quantity in accordance with a symptom of a patient. After the medical licensee removes air from the portable painkilling system, it is attached to a patient's body, and the outlet portion of the portable painkilling system is coupled to a catheter communicated to the interior of the patient's body. At this time, liquid medicine has already started to inject liquid medicine continuously from the first continuous injector for liquid medicine into the reservoir. Meanwhile, the patient can move freely while wearing the system on the patient's body. When a given amount of liquid medicine is charged in the reservoir, flow of liquid medicine from the first continuous injector is automatically stopped due to a pressure of liquid medicine in the reservoir. After the patient confirms that the reservoir is filled with liquid medicine, the patient presses the reservoir to transfer liquid medicine from the reservoir to the second continuous injector. Then, the second continuous injector begins to continuously inject liquid medicine into the interior of the patient's body. On the other hand, liquid medicine is charged from the first continuous injector into the empty reservoir. This operation is repeated several times over a long period of time until the first continuous injector becomes empty.

For preparation of a next pain, a patient can receive a supplemental liquid medicine in the reservoir at a hospital or in the home by a medical licensee.

BEST MODE FOR CARRYING OUT THE INVENTION

An example of a portable painkilling system in accordance with the present invention will be explained below by referring now to FIGS. 1 to 8.

Figure 1:
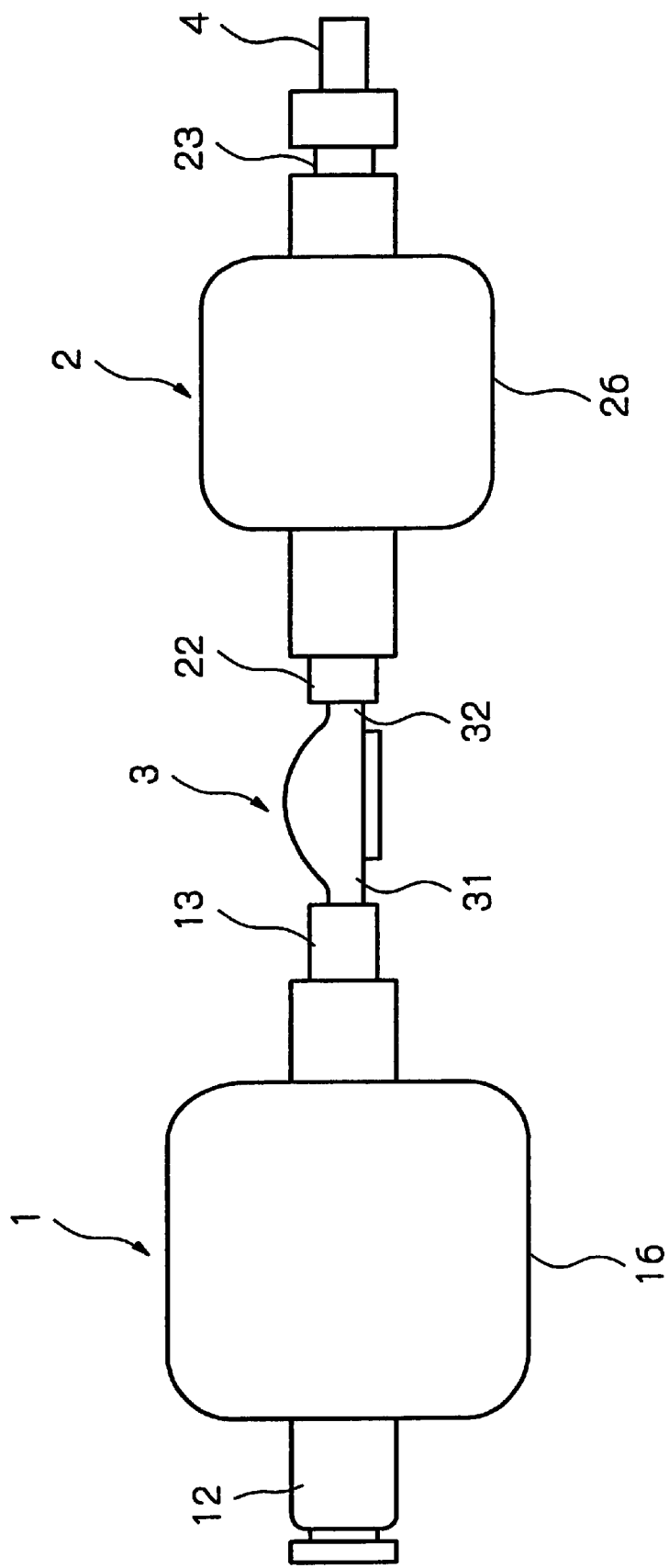
FIG. 1 is a plan view of a portable painkilling system in accordance with the present invention.
Figure 2:
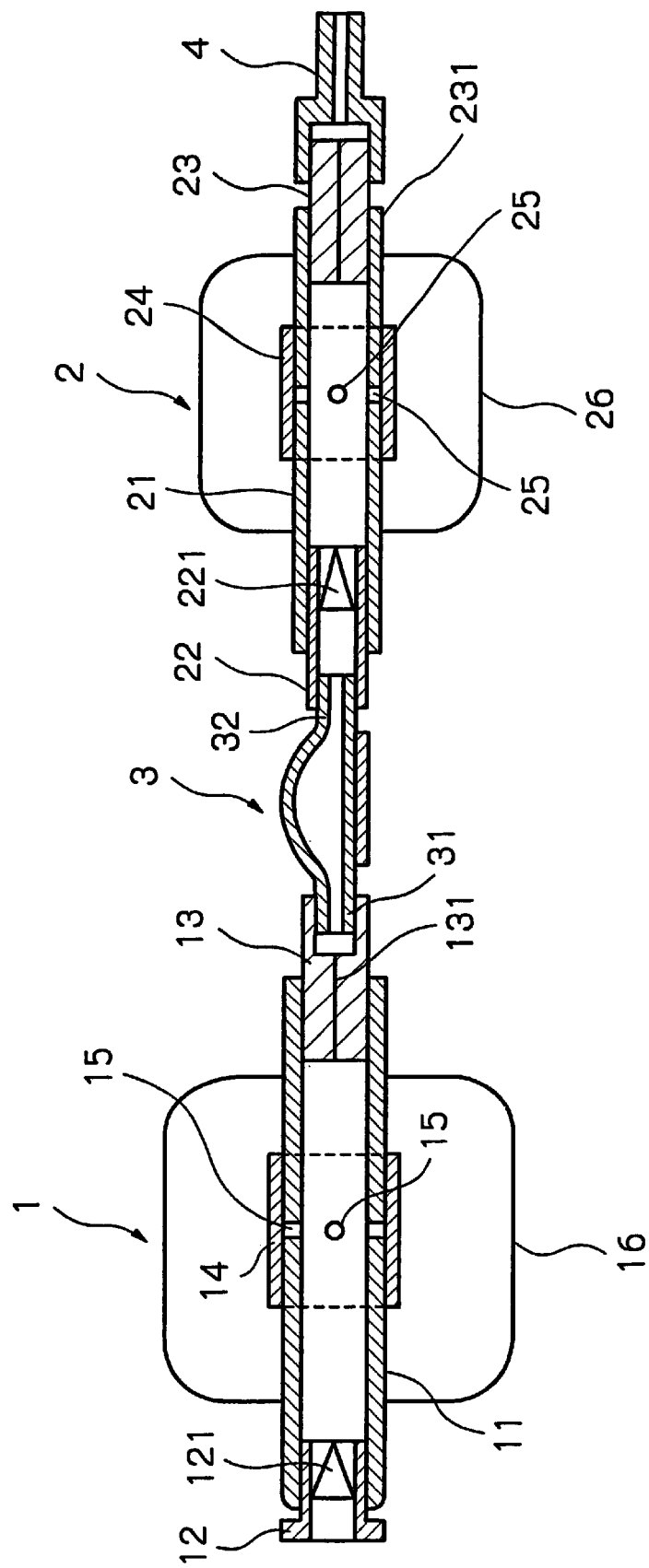
FIG. 2 is a longitudinal section view of FIG. 1.

As shown in FIGS. 1 and 2, a portable painkilling system of the present invention comprises: a first continuous injector 1 for liquid medicine which continuously discharges liquid medicine through a control path 131 in an outlet portion 13 for a given period of time; a flexible, elastic reservoir 3 connected to the outlet portion 13 of the first continuous injector 1 for liquid medicine at one end thereof, the reservoir 3 being adapted to constrict in a normal condition and to expand when liquid medicine from the first continuous injector 1 is being charged into the reservoir 3 so as to contain a maximum quantity of liquid medicine; and a second continuous injector 2 for liquid medicine having an inlet portion 22 connected to the other end 32 of the reservoir 3, the second continuous injector 2 being adapted to receive liquid medicine from the reservoir 3 and to continuously discharge liquid medicine stored in the second continuous injector 2 through a control path 231 in an outlet portion 23 for a given period of time.

A male lure connector 4 is connected to the outlet portion 23 of the second continuous injector 2 for liquid medicine 2 while a conventional catheter (not shown) is connected to the male lure connector 4. The catheter is connected to a patient's body.

As the first and second continuous injectors 1 and 2 for liquid medicine, an injector developed by the present applicant (Japanese Patent No. 1384289) may be utilized in this invention. This injector includes inlet and outlet portions for liquid medicine and a balloon which connects the inlet portion to the outlet portion. Liquid medicine injected in the balloon flows out through the outlet portion for a long period of time.

The first continuous injector 1 for liquid medicine, as shown in FIG. 2, is provided on opposite ends of a cylindrical body 11 with an inlet portion 12 for liquid medicine and an outlet portion 13 for liquid medicine, respectively. A balloon 14 is attached to an outer periphery of the cylindrical body 11. An interior of the balloon 14 is communicated with an interior of the cylindrical body 11 through a communication hole 15. The cylindrical body 11 may be omitted and the inlet portion 12 and outlet portion 13 may be directly interconnected through the balloon 14.

The inlet portion 12 is provided with a check valve 121 which prevents injected liquid medicine from flowing in a reverse direction. The balloon 14 is made of an elastic material and can accommodate a given amount of liquid medicine (in this embodiment, for example, 40 to 250 cubic centimeters). The outlet portion 13 is provided with a control path 131 which controls an outflow period of time for liquid medicine (for example, 0.5 to 10 hours).

In order to protect the inflated balloon 14 against an external force, a safety cover 16 is attached to the injector 1.

The second continuous injector 2 for liquid medicine has a structure similar to that of the first continuous injector 1. That is, the second continuous injector 2, as shown in FIG. 2, is provided on opposite ends of a cylindrical body 21 with an inlet portion 22 for liquid medicine and an outlet portion 23 for liquid medicine, respectively. A balloon 24 is attached to an outer periphery of the cylindrical body 21. An interior of the, balloon 24 is communicated with an interior of the cylindrical body 21 through a communication hole 25. The cylindrical body 21 may be omitted and the inlet portion 22 and outlet portion 23 may be directly interconnected through the balloon 24.

The inlet portion 22 is provided with a check valve 221 which prevents injected liquid medicine from flowing in a reverse direction. The check valve 221 is opened at a pressure higher than a maximum inner pressure in the first continuous injector 1 for liquid medicine. Preferably, the check valve 221 may be a valve such as a duckbill valve, an umbrella valve, or the like.

The balloon 24 is made of an elastic material and can accommodate a given amount of liquid medicine (in this embodiment, for example, 1 to 5 cubic centimeters). The outlet portion 23 is provided with a control path 231 which controls an outflow period of time for liquid medicine (for example, 0.5 to 10 hours).

Figure 8:
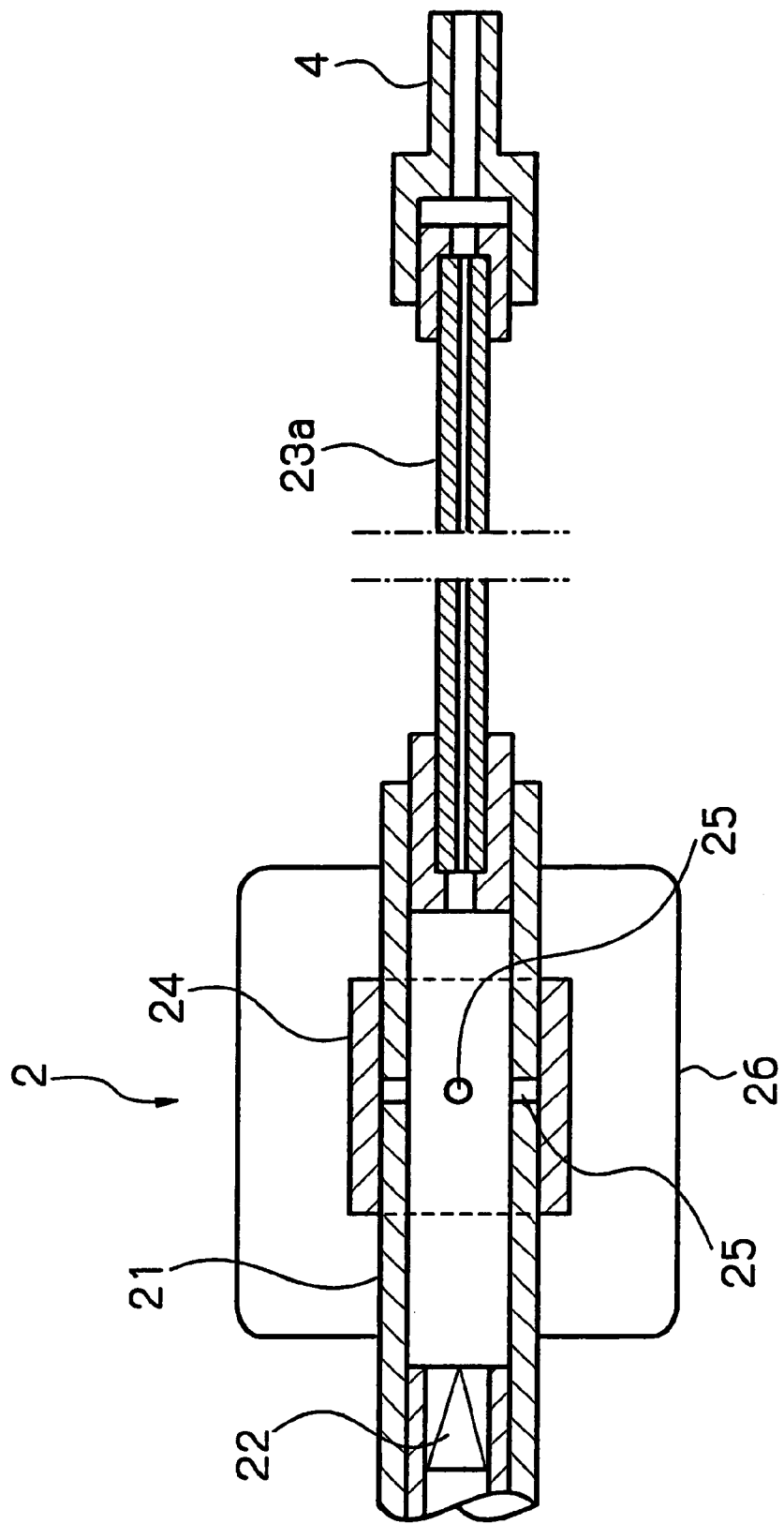
FIG. 8 is a partial longitudinal section view of an alteration of a second continuous injector for liquid medicine.

As shown in FIG. 8, the outlet portion 23 may be an elongated flexible tube 23a having a length of 20 to 1000 mm and an inner diameter of 0.1 to 0.5 mm.

In order to protect the inflated balloon 24 against an external force, a safety cover 26 is attached to the injector 1.

The male lure 4 may be an article freely available and sold on the market.

The reservoir 3 may be a flexible, elastic reservoir which is adapted to constrict in a normal condition and to expand when liquid medicine from the first continuous injector 1 is being charged into the reservoir so as to contain a maximum quantity of liquid medicine (in this embodiment, for example, 3 to 5 cubic centimeters). A preferable reservoir 3 suitable for the portable painkilling system of the present invention is any one of. various kinds of reservoir, as shown in FIGS. 7(A) to 7(G), a syringe type reservoir (A), a bag type reservoir (B), a bellows type reservoir (C), a circular button type reservoir (D), a dome type reservoir (E), a multi-stepped, button type reservoir (F), a tandem chamber type reservoir (G) or the like.

In this embodiment, the reservoir 3 is designed to have a maximum volume of about 3 to 5 cubic centimeters, a maximum pressure of about 300 to 450 mm Hg, and a maximum discharge period of time of about 20 to 60 seconds.

Next, an operation of the portable painkilling system in accordance with the present invention will be explained by referring to FIGS. 1 to 6.

First, as shown in FIG. 1, the first and second continuous injectors 1 and 2 for liquid medicine which have given volumes and a continuous discharge period of time, respectively, the reservoir 3 having a given volume, and the male lure connector 4 have already been sterilized and disinfected for preparation of assembling. The first continuous injector 1 for liquid medicine, the reservoir 3, the second continuous injector 2 for liquid medicine, the: male lure connector 4 are connected in series one after another.

Figure 3:
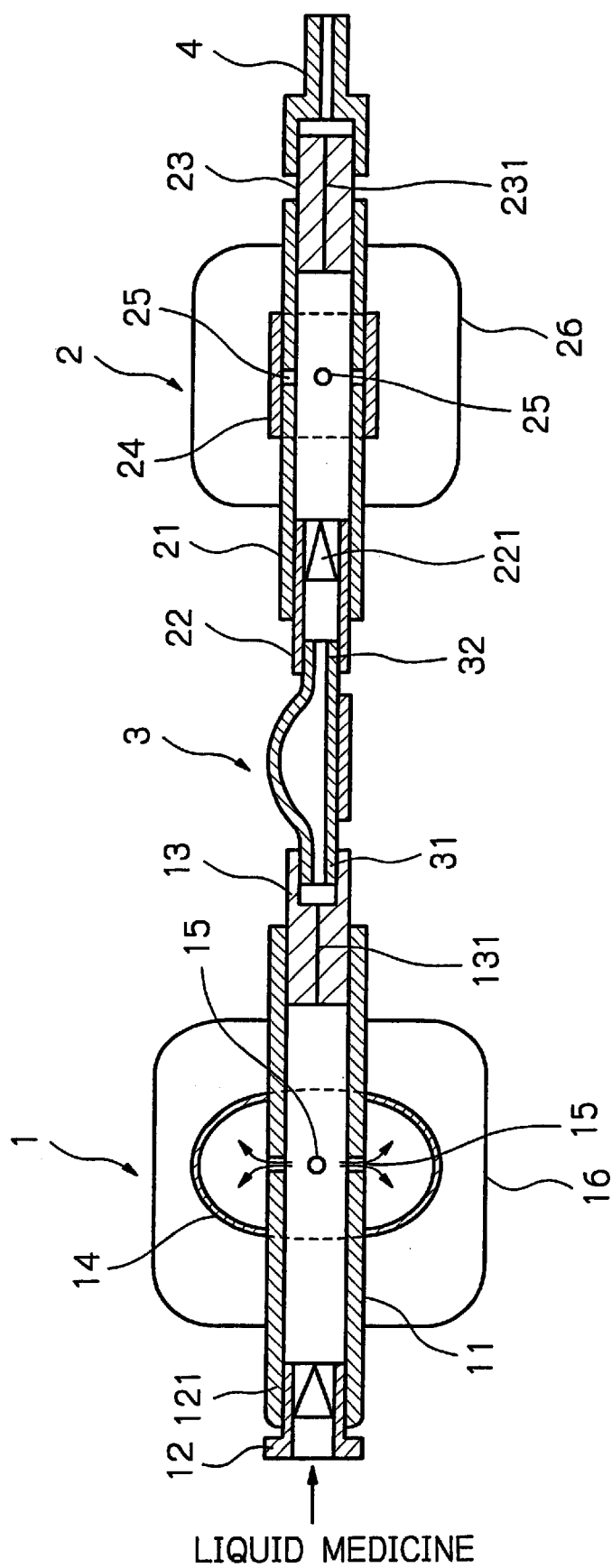
FIG. 3 is an explanatory view illustrating an operation of charging liquid medicine into a first continuous injector for liquid medicine.

Second, a medical licensee charges a given quantity of liquid medicine into the first continuous injector 1 in accordance with the symptoms of a patient. For example, as shown in FIG. 3, a given amount of liquid medicine (for: example, physiological saline, grape sugar solution, antibiotic substance, calmative, analgesic, heparin, nitroglycerin solution, or the like) is charged into the continuous injector 1 through the inlet portion 12 by a syringe (not shown) or the like. It is possible to use a first continuous injector 1 in which liquid medicine has been charged beforehand. It is also possible to charge liquid medicine into the injector 1 after attaching the present system to a patient's body.

After the medical licensee removes air from the portable painkilling system, it is attached to a patient's body, and the male lure connector 4 connected to the outlet portion 23 of the portable painkilling system is coupled to a catheter (not shown) communicated to the interior of the patient's body.

Figure 4:
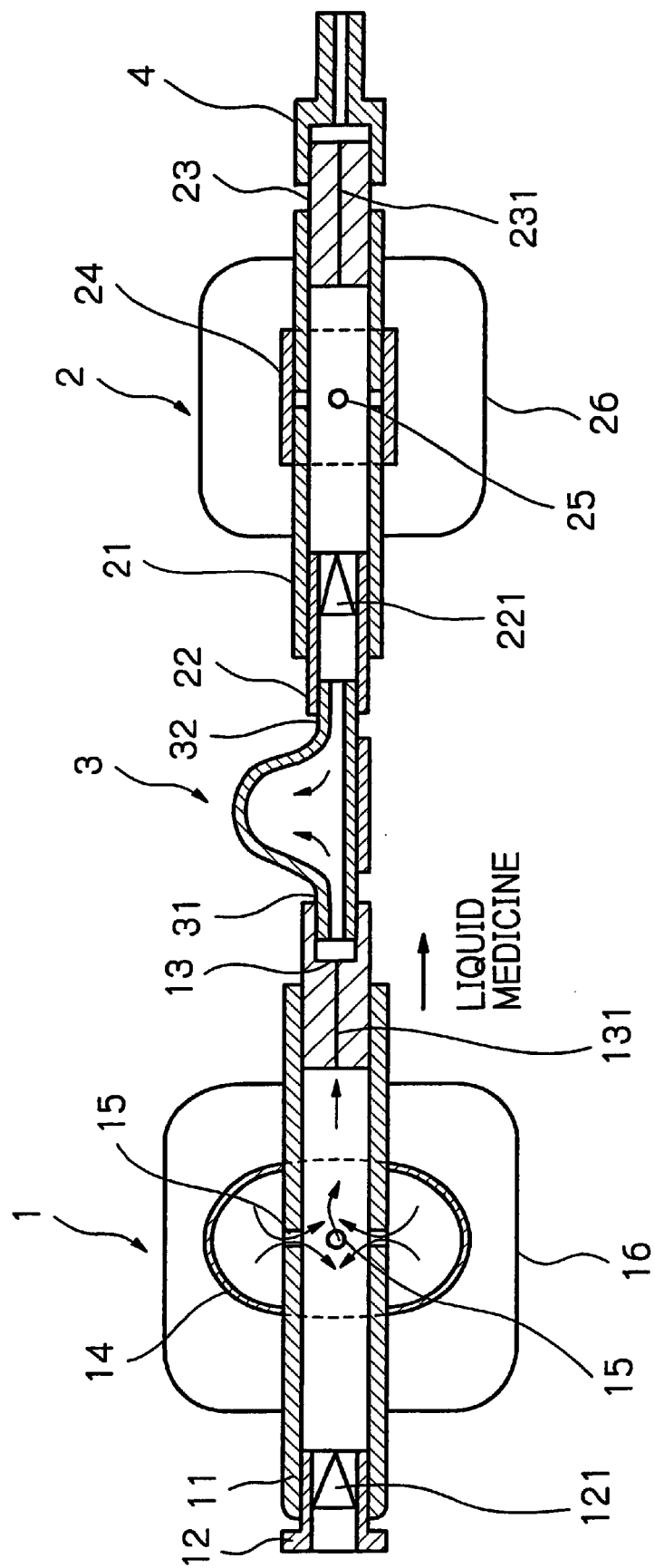
FIG. 4 is an explanatory view illustrating an operation of charging liquid medicine from a first continuous injector to a reservoir.

At this time, liquid medicine has already started to continuously flow from the first continuous injector 1 into the reservoir 3 by means of a contraction force of the balloon 14, as shown in FIG. 4. Meanwhile, the patient can move freely while wearing the system on the patient's body.

Figure 5:
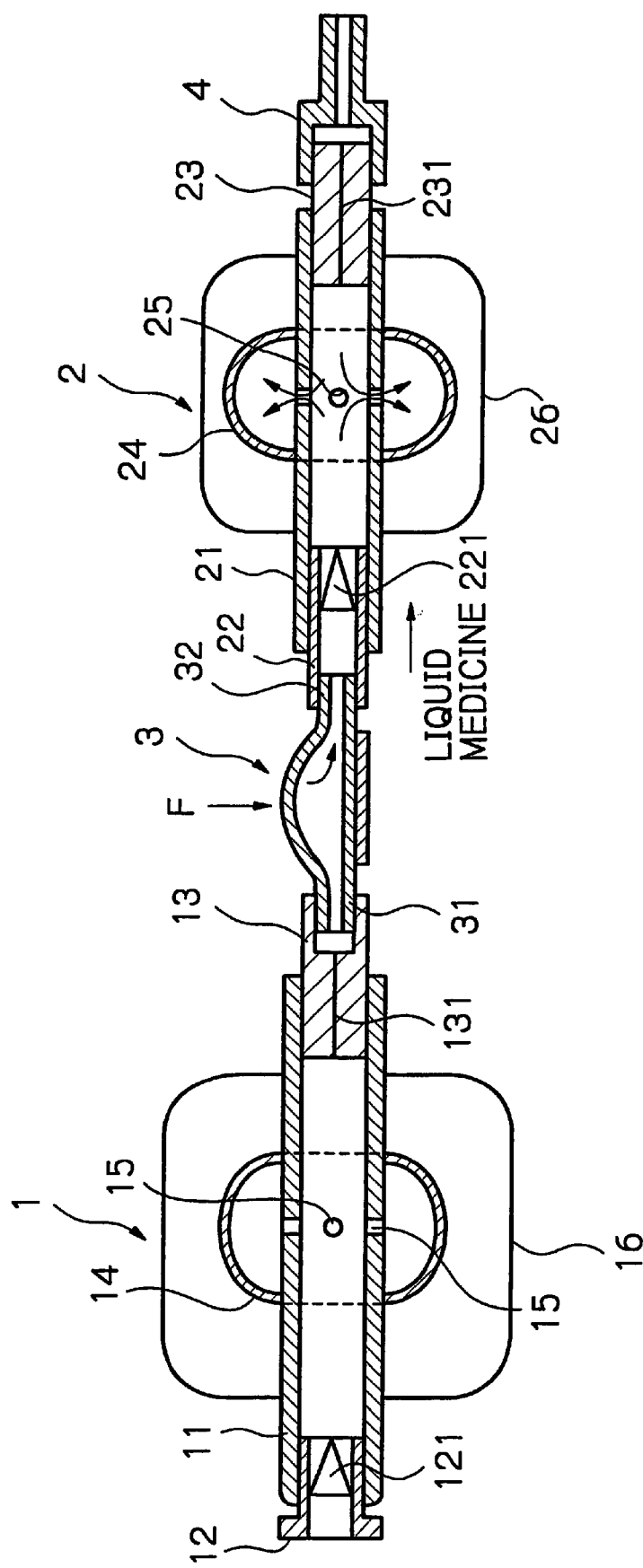
FIG. 5 is an explanatory view illustrating an operation of charging liquid medicine from a reservoir to a second continuous injector.

When a given amount of liquid medicine is charged in the reservoir 3, flow of liquid medicine from the first continuous injector 1 is automatically stopped due to a closing pressure exerted in the check valve 221 (see FIG. 5).

After the patient confirms that the reservoir 3 is fully filled with liquid medicine, the patient presses the reservoir 3 with a force F to transfer liquid medicine from the reservoir 3 to the second continuous injector 2, as shown in FIG. 5.

Figure 6:
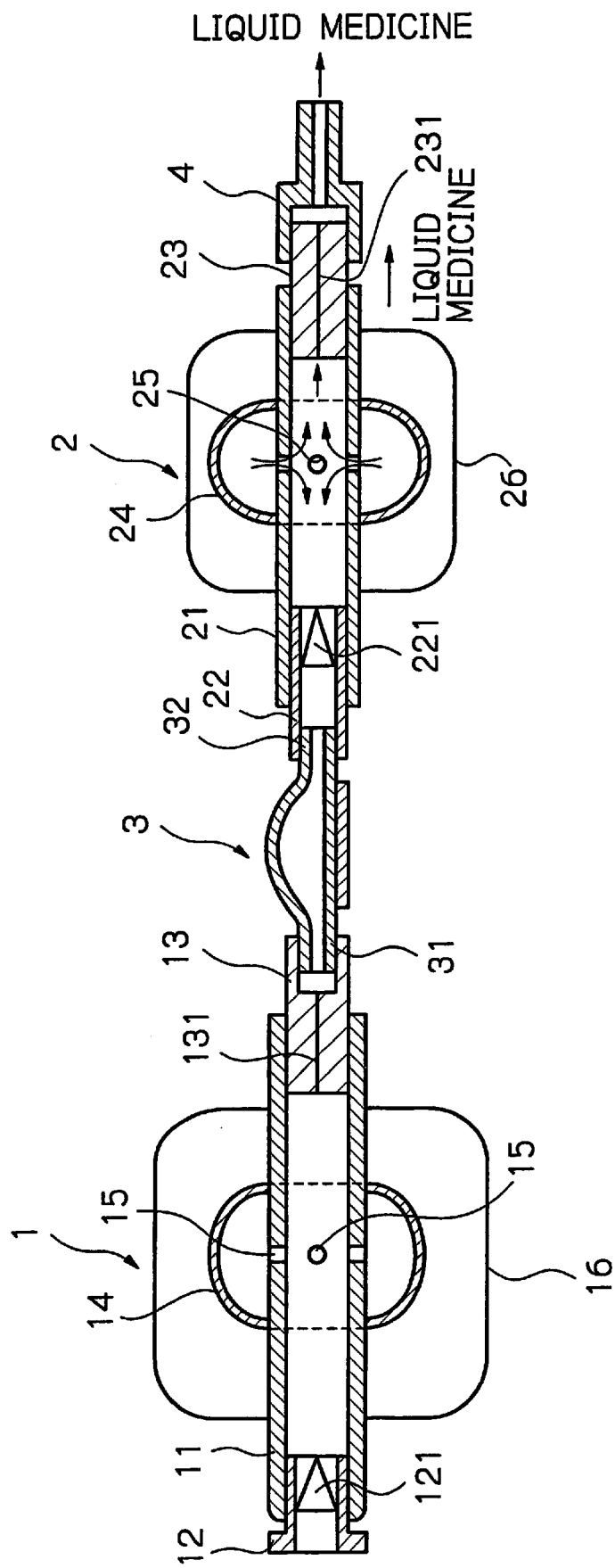
FIG. 6 is an explanatory view illustrating an operation of discharging liquid medicine out of the system.
Figure 7:
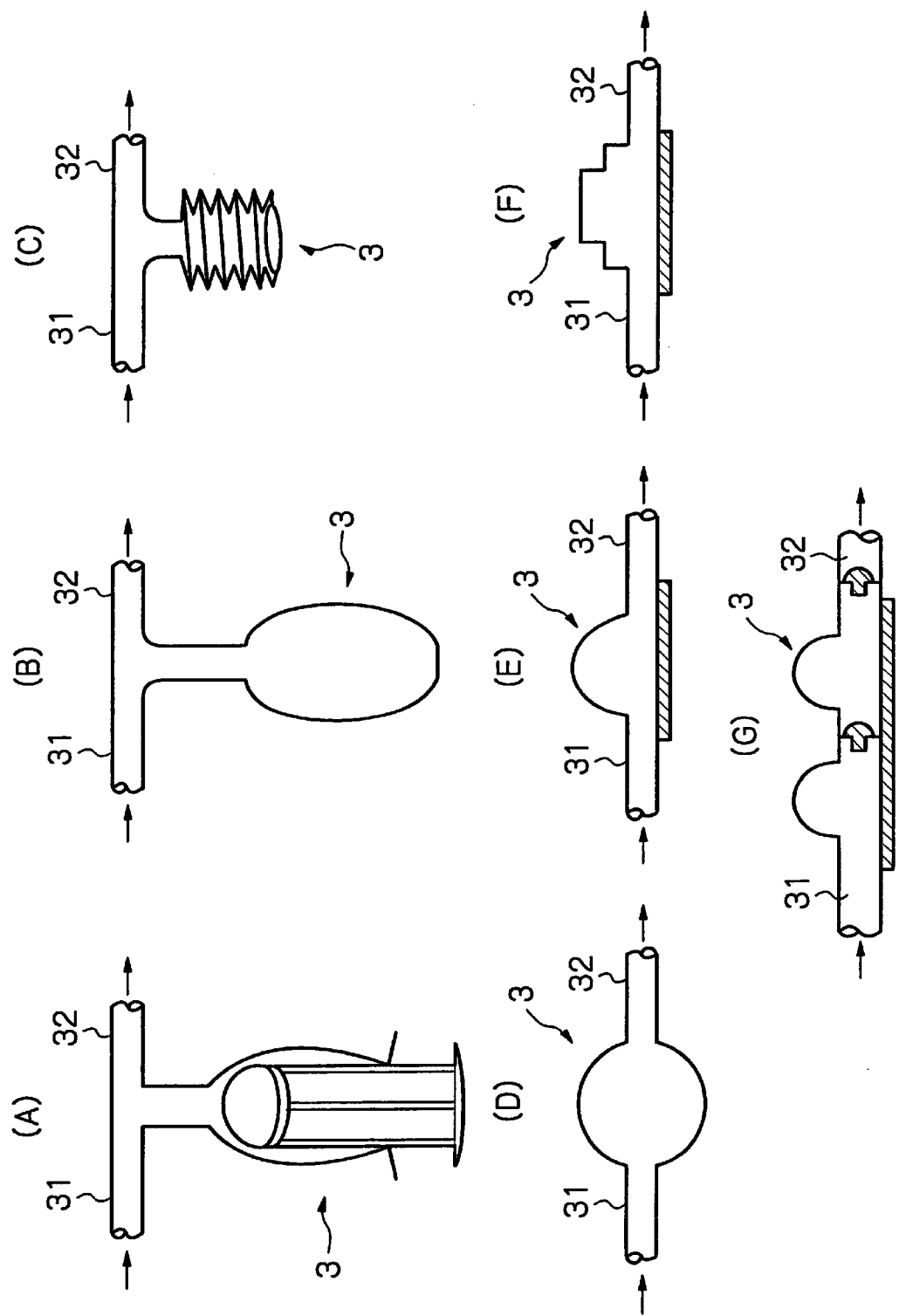
FIGS. 7(A) to 7(G) are longitudinal section views, of various kinds of reservoir to be used in the present invention, FIG. 7(A) illustrating a syringe type reservoir, FIG. 7(B) illustrating a bag type reservoir, FIG. 7(C) illustrating a bellows type reservoir, FIG. 7(D) illustrating a circular button type reservoir, FIG. 7(E) illustrating a dome type reservoir, FIG. 7(F) illustrating a multi-stepped, button type reservoir, and FIG. 7(G) illustrating a tandem chamber type reservoir, respectively.

Then, as shown in FIG. 6, the second continuous injector 2 begins to continuously inject liquid medicine into the interior of the patient's body. On the other hand, liquid medicine is charged from the first continuous injector 1 into the empty reservoir 3.

This operation is repeated several times over a long period of time until the first continuous injector 1 becomes empty.

Volumes and continuous injection period of time in the first and second continuous injectors 1 and 2, and the volume of the reservoir may be selected beforehand in accordance with a symptom of a patient.

For preparation of a next pain, a patient can receive a supplemental liquid medicine in the reservoir at a hospital or in the home by a medical licensee.

Although the present system can be used again by repeating the above-mentioned operation, the first continuous injector 1 may be thrown away every time.

According to the present invention, since liquid medicine can be completely transferred from the reservoir 3 to the second continuous injector 2 by a simple pressing action by a patient, a control of liquid medicine becomes easy, an excessive dose of liquid medicine can be prevented, and thus a patient can use liquid medicine safely.

Industrial Applicability

The system of the present invention can be applied for first-aid treatment as well as chronic conditions including those involving terminal care. Also, it can be applied for sedation, detoxification, fever control, supply of nutrition, and the like as well as for analgesics.

What is claimed is:

1. A portable painkilling system comprising:
    a first continuous injector for liquid medicine which continuously discharges liquid medicine through a control path in an outlet portion for a given period of time wherein said first continuous injector has a first cylindrical body and a first balloon disposed therein, attached to the periphery of said cylindrical body;
    a flexible, elastic reservoir connected to said outlet portion of said first continuous injector for liquid medicine at one end thereof, said reservoir being adapted to constrict in a normal condition and to expand when liquid medicine from said first continuous injector is being charged into said reservoir so as to contain a maximum quantity of liquid medicine; and
    a second continuous injector for liquid medicine having an inlet portion connected to the other end of said reservoir, said second continuous injector being adapted to receive liquid medicine from said reservoir and to continuously discharge liquid medicine stored in said second continuous injector through a control path in an outlet portion for a given period of time, and wherein said second continuous injector has a second cylindrical body and a second balloon disposed therein, attached to the periphery of said cylindrical body.

2. A portable painkilling system according to claim 1, wherein said outlet portion is made of an elongate flexible tube having a small inner diameter.

3. A portable painkilling system according to claim 1 or 2, wherein said reservoir is a syringe type reservoir.

4. A portable painkilling system according to claim 1 or 2, wherein said reservoir is a bag type reservoir.

5. A portable painkilling system according to claim 1 or 2, wherein said reservoir is a bellows type reservoir.

6. A portable painkilling system according to claim 1 or 2, wherein said reservoir is a circular button type reservoir.

7. A portable painkilling system according to claim 1, wherein said reservoir is a dome type reservoir.

8. A portable painkilling system according to claim 1 or 2, wherein said reservoir is a multi-stepped, button type reservoir.

9. A portable painkilling system according to claim 1 or 2, wherein said reservoir is a tandem chamber type reservoir.

* * * * *